US010438338B2

(12) United States Patent
Ding et al.

(10) Patent No.: US 10,438,338 B2
(45) Date of Patent: Oct. 8, 2019

(54) LIGHT LINE IMAGER-BASED IC TRAY POCKET DETECTION SYSTEM

(71) Applicant: Delta Design, Inc., Poway, CA (US)

(72) Inventors: Kexiang Ken Ding, San Diego, CA (US); James Frandsen, Ramona, CA (US); Chris Do, Poway, CA (US)

(73) Assignee: Delta Design, Inc., Poway, CA (US)

( * ) Notice: Subject to any disclaimer, the term of this patent is extended or adjusted under 35 U.S.C. 154(b) by 144 days.

(21) Appl. No.: 15/664,504

(22) Filed: Jul. 31, 2017

(65) Prior Publication Data

US 2018/0033137 A1 Feb. 1, 2018

Related U.S. Application Data

(60) Provisional application No. 62/369,446, filed on Aug. 1, 2016.

(51) Int. Cl.
| | | |
|---|---|---|
| *G01S 17/46* | (2006.01) | |
| *H01L 21/67* | (2006.01) | |
| *H01L 21/673* | (2006.01) | |
| *G01N 21/88* | (2006.01) | |
| *G01N 21/956* | (2006.01) | |
| *G06T 7/00* | (2017.01) | |

(Continued)

(52) U.S. Cl.
CPC ....... *G06T 7/0008* (2013.01); *G01N 21/8851* (2013.01); *G01S 17/026* (2013.01); *G01S 17/46* (2013.01); *G06T 7/70* (2017.01); *H01L 21/67259* (2013.01); *H01L 21/67333* (2013.01); *G01N 2021/95638* (2013.01); *G06T 2207/30148* (2013.01); *G06T 2207/30204* (2013.01)

(58) Field of Classification Search
None
See application file for complete search history.

(56) References Cited

U.S. PATENT DOCUMENTS

| | | |
|---|---|---|
| 5,000,573 A | 3/1991 | Suzuki et al. |
| 5,463,227 A | 10/1995 | Stern et al. |
| 8,041,533 B2 | 10/2011 | Ding et al. |

(Continued)

FOREIGN PATENT DOCUMENTS

| | | |
|---|---|---|
| EP | 0 445 651 A2 | 9/1991 |
| WO | WO-2012/176623 A1 | 12/2012 |

OTHER PUBLICATIONS

International Search Report and Written Opinion dated Nov. 7, 2017 in PCT/US2017/044632 (15 pgs.).

*Primary Examiner* — Idowu O Osifade
(74) *Attorney, Agent, or Firm* — Foley & Lardner LLP (57) ABSTRACT

A system for detecting a status of a pocket of a tray includes a tray having a plurality of pockets that hold an integrated circuit device, a vision mechanism, a light line generator, a reflective device, and a controller. The vision mechanism images the tray along a first optical axis. The light line generator emits a light line along a second optical axis. The reflective device reflects the light line onto the tray along a third optical axis. The third optical axis has a different angle relative to the first optical axis than an angle between the first optical axis and the second optical axis. The controller receives an image of the tray from the vision mechanism, detects the light line reflected onto the tray along the third optical axis, and determines a status of a pocket based on the detected light line along the third optical axis.

24 Claims, 8 Drawing Sheets

(51) Int. Cl.
  *G06T 7/70*   (2017.01)
  *G01S 17/02*  (2006.01)

(56) References Cited

U.S. PATENT DOCUMENTS

| | | | |
|---|---|---|---|
| 2003/0039388 A1* | 2/2003 | Ulrich | G01B 11/2513 |
| | | | 382/145 |
| 2005/0008218 A1* | 1/2005 | O'Dell | G01N 21/9501 |
| | | | 382/145 |
| 2005/0199782 A1 | 9/2005 | Calver et al. | |
| 2009/0281762 A1 | 11/2009 | Ding et al. | |

* cited by examiner

LIGHT LINE IMAGER-BASED IC TRAY POCKET DETECTION SYSTEM

CROSS-REFERENCE TO RELATED APPLICATIONS

The present application claims priority to U.S. Provisional Application No. 62/369,446, filed on Aug. 1, 2016, the disclosure of which is hereby incorporated by reference in its entirety.

FIELD

The present disclosure generally relates to a detection system for a device tray of an integrated circuit ("IC") device test handler system. In particular, the present disclosure relates to a camera and light line-based detection system for on-the-fly detection of a placement of a device in a tray pocket.

BACKGROUND

During testing of an IC device, one or more devices may be placed in one or more pockets of a tray, such as a JEDEC tray. A detection system may be used to determine a status of a given pocket in the tray, such as whether the pocket is empty, contains a properly placed device, or contains a stack of devices. In some detection systems, such as that disclosed in U.S. Pat. No. 8,041,533, a dual-cross, angled laser and a camera system may be used. However, the use of multiple lasers and a static detection system increases the space needed for the detection system in an already limited-space environment.

SUMMARY

In one embodiment, a system for detecting a status of a pocket of a tray includes a tray having a plurality of pockets that hold an integrated circuit device, a vision mechanism, a light line generator, a reflective device, and a controller. The vision mechanism images the tray along a first optical axis. The light line generator emits a light line along a second optical axis. The reflective device reflects the light line onto the tray along a third optical axis. The third optical axis has a different angle relative to the first optical axis than an angle between the first optical axis and the second optical axis. The controller receives an image of the tray from the vision mechanism, detects the light line reflected onto the tray along the third optical axis, and determines a status of a pocket based on the detected light line along the third optical axis.

In one aspect, the plurality of pockets is arranged in a plurality of rows and a plurality of columns and the light along the third optical axis is reflected along a row of the plurality of rows.

In one aspect, the tray also includes a first outer protrusion provided at a first end of the plurality of rows and a second outer protrusion provided at a second end of the plurality of rows. The first and second outer protrusions are formed along a length of the plurality of columns.

In one aspect, the controller further detects the light line along the third optical axis reflected onto the first outer protrusion and the second outer protrusion, detects the light line along the third optical axis reflected onto a surface of the pocket, calculates an offset between the detected light line on the first outer protrusion and the second outer protrusion and the detected light line on the surface of the pocket, and determines the status of the pocket based on the calculated offset.

In one aspect, the controller further sets an upper limit position of the light line along the third optical axis reflected on the surface of the pocket, sets a lower limit position of the light line along the third optical axis reflected on the surface of the pocket, and detects a shift of the light line along the third optical axis. The status of the pocket is determined based on the detected shift.

In one aspect, the first outer protrusion and the second outer protrusion are provided with at least one notch such that at least one row of the plurality of rows comprises the at least one notch at an end of the at least one row. The controller further interpolates a position of the light line along the third optical axis reflected onto the at least one notch based on one or more positions of the detected light line along the third optical axis reflected onto the first outer protrusion or the second outer protrusion of one or more rows adjacent to the at least one row.

In one aspect, the controller interpolates the position of the light line along the third optical axis reflected onto the at least one notch based on an average of a first position of the detected light line along the third optical axis reflected onto the first outer protrusion or the second outer protrusion of a first adjacent row and a second position of the detected light line along the third optical axis reflected onto the first outer protrusion or the second outer protrusion of a second adjacent row.

In one aspect, the status of the pocket is one of an integrated device properly placed in the pocket, a stack of two or more integrated devices placed in the pocket, an integrated device partially placed in the pocket, or an empty pocket.

In one aspect, the light line generator is a laser.

In one aspect, the second optical axis is substantially parallel to the first optical axis.

In one aspect, the first optical axis and the second optical axis are substantially orthogonal to an upper surface of the tray.

In one aspect, the third optical axis is offset from the first optical axis by an angle of about 35 degrees to about 55 degrees.

In one aspect, the third optical axis is offset from the first optical axis by an angle of 45 degrees.

In one aspect, the laser is mounted to the vision mechanism.

In one aspect, the laser is mounted to a pick-and-place device configured to place a plurality of integrated circuit devices into the plurality of pockets of the tray. The reflective device is configured to reflect the light line onto the tray along the third optical axis such that the space required to mount the laser to the pick-and-place device is reduced.

In one aspect, the tray is a JEDEC tray.

In another embodiment, a method for detecting a status of a pocket of a tray includes providing a tray having a plurality of pockets that hold an integrated circuit device, providing a vision mechanism that images the tray along a first optical axis, emitting a light line along a second optical axis, reflecting the light line onto the tray along a third optical axis, the third optical axis having a different angle relative to the first optical axis than an angle between the first optical axis and the second optical axis, receiving at a controller an image of the tray from the vision mechanism, detecting the light line reflected onto the tray along the third optical axis, and determining a status of a pocket based on the detected light line along the third optical axis.

In one aspect, the method further includes setting an upper limit position of the light line reflected along the third optical axis projected onto the pocket, and setting a lower limit position of the light line reflected along the third optical axis projected onto the pocket. The step of determining a status of a pocket includes detecting a shift of the light line reflected along the third optical axis.

In one aspect, the third optical axis is offset from the second optical axis by an angle of about 35 degrees to about 55 degrees.

In one aspect, the second optical axis is substantially orthogonal to an upper surface of the tray.

In one aspect, the tray includes a plurality of rows and a plurality of columns, and the light line having the third optical axis is reflected along a row of the plurality of rows.

In one aspect, the step of reflecting the light line onto the tray along a third optical axis includes reflecting a light line having the third optical axis along a first row of the plurality of rows. The step of detecting the light line reflected onto the tray along the third optical axis includes detecting the light line having the third optical axis along the first row. The step of determining a status of a pocket includes determining a status of each of the plurality of pockets in the first row based on the detected light line reflected along the first row. The steps of reflecting the light line, detecting the light line, and determining a status of a pocket are repeated for each row of the plurality of rows.

In one aspect, the tray further includes a first outer protrusion disposed at a first end of the plurality of rows and a second outer protrusion disposed at a second end of the plurality of rows, the first and second outer protrusions extending along a length of the plurality of columns.

In one aspect, the step of detecting the light line reflected onto the tray includes detecting the light line reflected along the third optical axis projected onto the first outer protrusion and the second outer protrusion, and the step of determining a status of a pocket includes calculating an offset between the detected light line on the first outer protrusion and the second outer protrusion and the detected light line on the pocket.

DETAILED DESCRIPTION

Embodiments of the present invention will be described below with reference to the accompanying drawings. It would be understood that the following description is intended to describe exemplary embodiments of the invention, and not to limit the invention.

Referring generally to the figures, the present disclosure provides a detection system capable of detecting a status of a pocket of a tray for a test handler system during runtime. The detection system utilizes a vision mechanism, a single light-emitting device, and a reflective device. The reflective device is positioned to reflect light emitted from the light-emitting device such that the emitted light is projected onto the tray for detection of a pocket by the vision mechanism. By reflecting light emitted from the light-emitting device, the reflective device allows the light-emitting device to be mounted such that the optical axis of the light-emitting device is substantially parallel to the optical axis of the vision mechanism. This allows the light-emitting device to be mounted on or near the vision mechanism and/or to be mounted on or near a handler pick-and-place device, minimizing the space needed to mount the light-emitting device and the overall space needed for the detection system.

Figure 1:
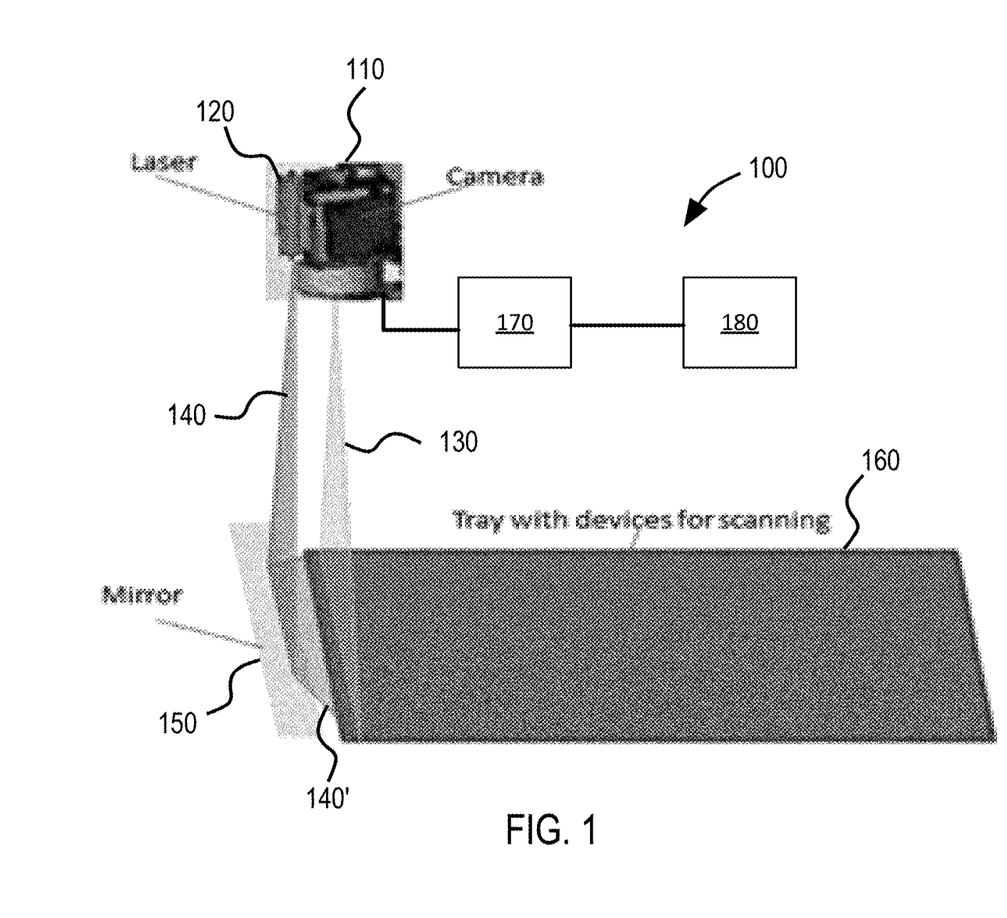
FIG. 1 is a schematic view of a detection system, according to one embodiment.

FIG. 1 shows a schematic view of a detection system 100 for a test handler system according to one embodiment of the present invention. The detection system 100 includes a vision mechanism, such as a down-looking camera 110, and a light-emitting device, such as light line generator or laser 120. A controller 170 is operably connected to the camera 110 and is configured to analyze images captured by the camera 110 and store information generated by the image analysis. The controller 170 may be further connected to a user interface 180 for generating output to and/or receiving input from a user.

As shown in FIG. 1, the camera 110 visually detects a portion of a tray 160 along a first optical axis 130. The laser 120 provides a light emission, in the form of a light line or laser beam, along a second optical axis 140. The laser 120 is positioned such that the second optical axis 140 is substantially parallel to the first optical axis 130. In some embodiments, the laser 120 may be directly mounted on the camera 110 such that the second optical axis 140 is parallel to the first optical axis 130. In the embodiment shown in FIG. 1, the camera 110 and the laser 120 are positioned such that the first and second optical axes 130, 140 are substantially orthogonal to a top surface of the tray 160.

As further shown in FIG. 1, a reflective device, such as a mirror 150, is provided at one side of the tray 160. The mirror 150 is configured to reflect the laser beam emitted by the laser 120 such that the light emitted from the laser 120 changes from traveling along the second optical axis 140 to traveling along an optical axis having a different angle with respect to the first optical axis 130. For example, as shown in FIG. 1, the mirror 150 is configured to reflect the laser beam from the second optical axis 140 to a third optical axis 140' that is offset from the first optical axis 130 and/or the second optical axis 140 by about 45 degrees. In some embodiments, the third optical axis 140' may be offset from the first optical axis 130 and/or the second optical axis 140 by an angle between about 35 degrees to about 55 degrees.

Figure 2:
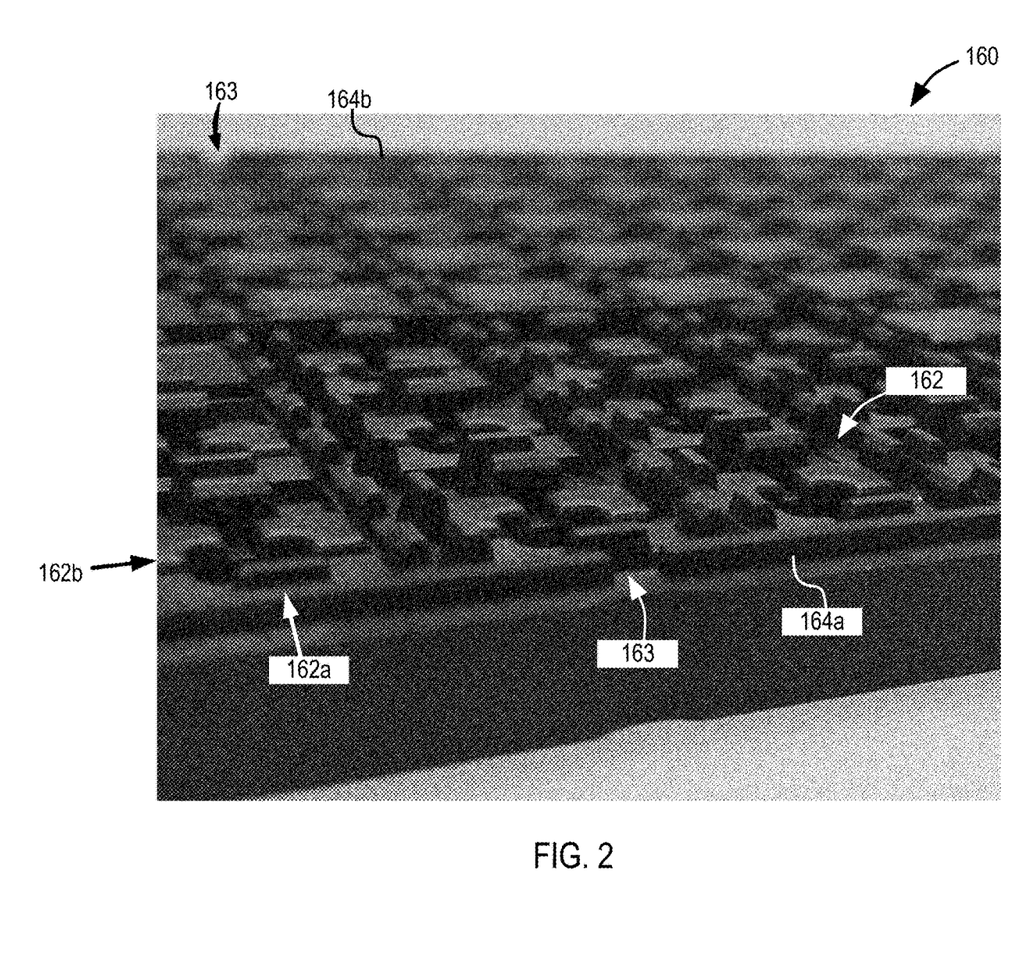
FIG. 2 is a detailed, perspective view of a tray, according to one embodiment.

As shown in FIG. 2, the tray 160 includes a plurality of pockets 162 that are each configured to hold a device (not shown in FIG. 2), such as an integrated circuit ("IC") or a semiconductor device. In certain embodiments, the tray 160 may be a JEDEC tray. The plurality of pockets 162 are arranged in a plurality of rows 162a and a plurality of columns 162b to form an array pattern. The number of pockets 162 in each of the plurality of rows is equal to the number of columns 162b. In some embodiments, the number of pockets 162 in the plurality of rows 162a is greater than or less than the number of pockets 162 in the plurality of columns 162b.

As further shown in FIG. 2, the tray 160 includes a first outer protrusion 164a provided at a first end of the rows 162a and a second outer protrusion 164b provided at a second end of the rows 162a. Both the first outer protrusion 164a and the second outer protrusion 164b run along a length of the columns 162b. In the embodiment shown in FIG. 2, one or more notches 163 are provided along lengths of the first and second shoulders 164a, 164b such that the lengths of the first and second shoulders 164a, 164b are discontinuous along the respective ends of the rows 162a.

The detection system 100 includes two processes when determining a status of a pocket 162 in a tray 160. First, the detection system 100 is configured to run through a training process in order to determine and store a trained pattern of the laser beam reflected along a given row 162a. Second, once the trained pattern has been stored for the tray 160, the detection system 100 then performs a runtime detection process to detect a status of a pocket 162 in the tray 160 during runtime of the test handler system.

Figure 3:
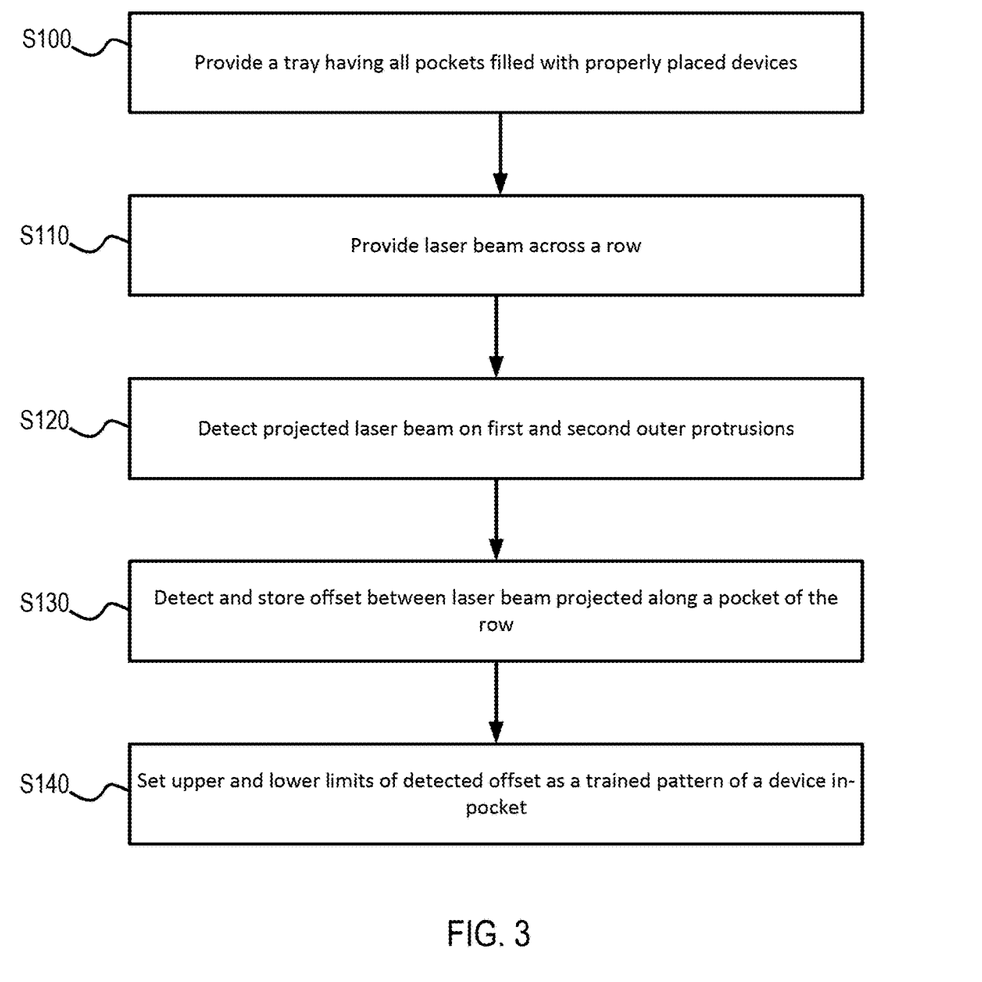
FIG. 3 is a flowchart showing a method for training the detection system of FIG. 1, according to one embodiment.
Figure 4:
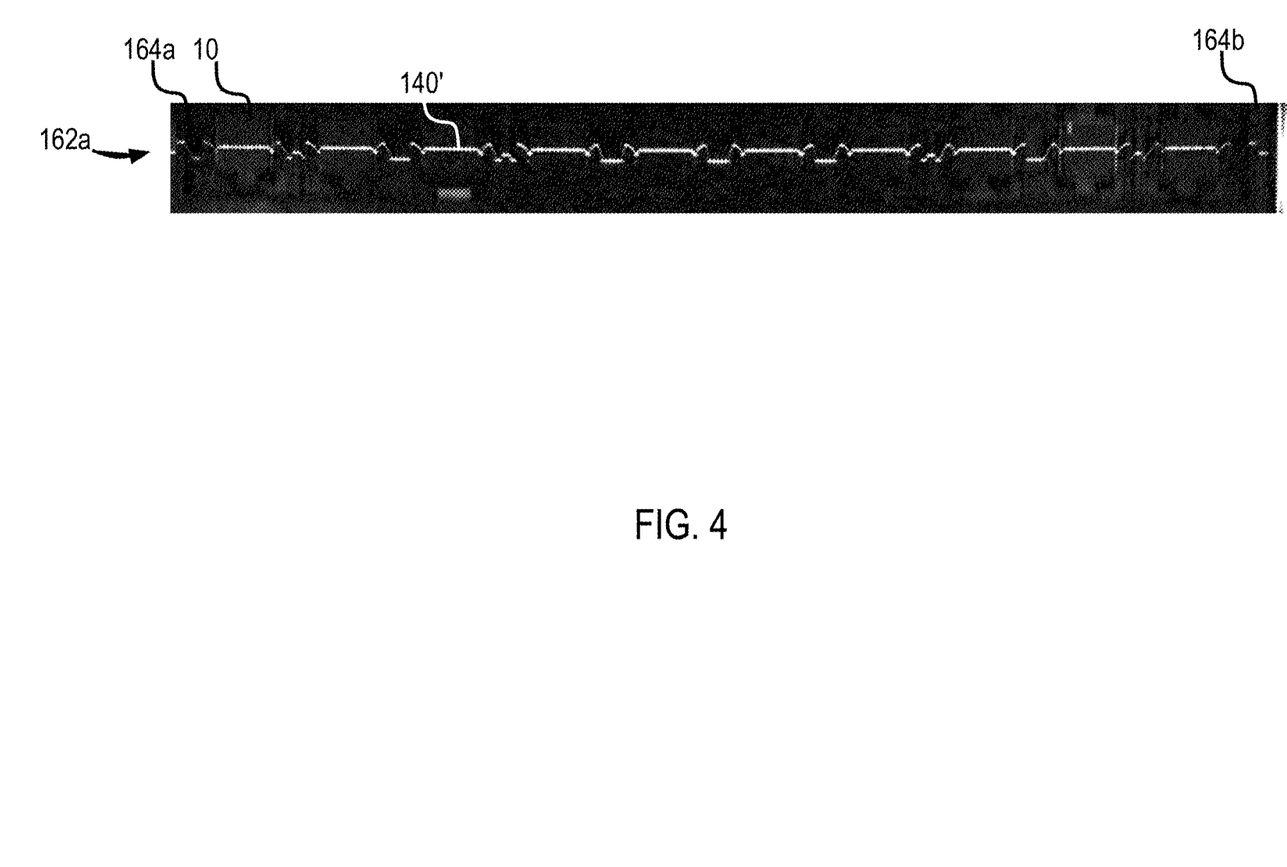
FIG. 4 is a top view of a light line projected onto a row of the tray using the detection system of FIG. 1.

FIG. 3 shows a flowchart of a method for determining and storing a trained pattern using the detection system 100 according to one embodiment of the present invention. As shown in FIG. 3, in a step S100, a tray 160 is provided where each of the pockets 162 includes a device 10 that is fully and properly placed or seated within the respective pocket. In a step S110, the detections system 100 projects a laser beam across one row 162a. During this step, the laser 120 emits the laser beam along the second optical axis 140, where it is reflected in the mirror 150 and offset to the third optical axis 140'. As shown in FIG. 4, the reflection results in the laser beam having the third optical axis 140' being projected across the one row 162a of the tray 160. In certain embodiments, the device 10 has a width that is equal to or greater than three times the width of the laser beam having the third optical axis 140' for reliable detection analysis.

In a step S120, the camera 110 captures the image of the laser beam projected across the row 162a, as shown in FIG. 4, and the controller 170 analyzes the image and detects the segments in which the laser beam is projected across each of the first and second outer protrusions 164a, 164b. These segments are then stored by the controller 170 as trained reference points for the row 162a. By storing the trained reference points for the row 162a based on the first and second outer protrusions 164a, 164b (in other words, reference is based on the tray shoulders rather than the shoulders of the individual pocket), pocket status detection is made possible even for small pocket trays.

Figure 5:
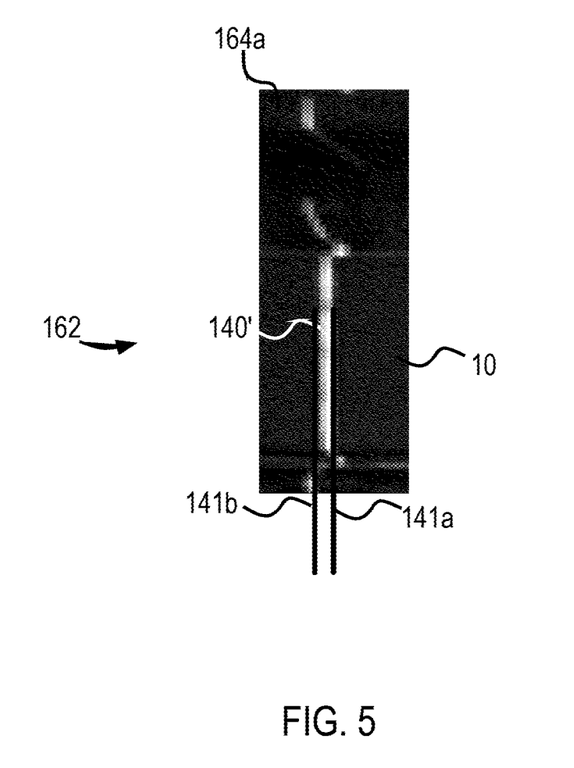
FIG. 5 is a training pattern stored in the detection system according to one embodiment.

In a step S130, the controller 170 then detects the segment in which the laser beam is projected across a pocket 162 having a device 10, as shown in FIG. 5. Once the segment is detected, the controller 170 calculates and stores an offset with regard to both line position and angle between the laser beam projected across the pocket 162 and the trained reference points determined from step S120. To provide a tolerance for the calculated offset, in a step S140, the user, using the user interface 180, may set an upper limit position 141a of the offset and a lower limit position 141b of the offset with respect to both line position and angle of the calculated offset. The set upper limit position 141a and the lower limit position 141b may be stored in the controller 180. The calculated offset and the set upper and lower limits 141b are stored as a trained pattern of an in-pocket device 10.

In some cases, lens distortions in the camera 110 and flatness errors in the upper surface of the tray 160 may cause variations in positions of the laser beam projected across each of the pockets 162 contained in a given row 162a. Thus, to account for these errors, the training process of FIG. 3 may be repeated for each pocket 162 in the given row 162a such that a trained pattern of an in-pocket device 10 is stored for each of the pockets 162 in the row 162a. Once an entire row 16a is trained, the detection system 100 may move the camera 110 and the laser 120 to an adjacent row 162a to continue the training process, where the process starts again at step S110.

As noted above, the first and second outer protrusions 164a, 164b may include one or more notches 163. In some cases, when a notch 163 is present at one or both ends of a row 162a that is being trained by the system 100, the laser beam having the third optical axis 140' may fail to be projected over the first and/or second outer protrusions 164a, 164b. In these cases, in order to train the row 162a having an adjacent notch 163 at one or both ends, the controller 170 interpolates one or more of the trained reference points for the row 162a based on the trained reference points for rows that are adjacent to the row 162a being trained. For example, the controller 170 may use a calculated average between the trained reference points stored for a previous row 162a and the trained reference points stored for a next row 162a. This calculated average may then be stored as trained reference points for the notch 163.

In addition, in some embodiments, the first row 162a that is trained by the system 100 is manually trained. When training the first row 162a, the user may manually train the controller 170 with the expected positions of the first and second outer protrusions 164a, 164b and the expected positions of the projected laser beam across the first and second outer protrusions 164a, 164b. The subsequent rows 162a may then be automatically trained by the controller 170 based on the manual train of the first row 162a.

Once the training of the system 100 is completed, runtime detection of the tray 160 may be performed. During runtime, the detection system 100 may be configured to continually detect a status of a pocket 162 in the tray 160 (e.g., a device 10 is properly placed in-pocket, a device 10 tilted within a pocket, two or more devices 10 are stacked within a pocket, no device 10 is contained within a pocket).

Figure 6:
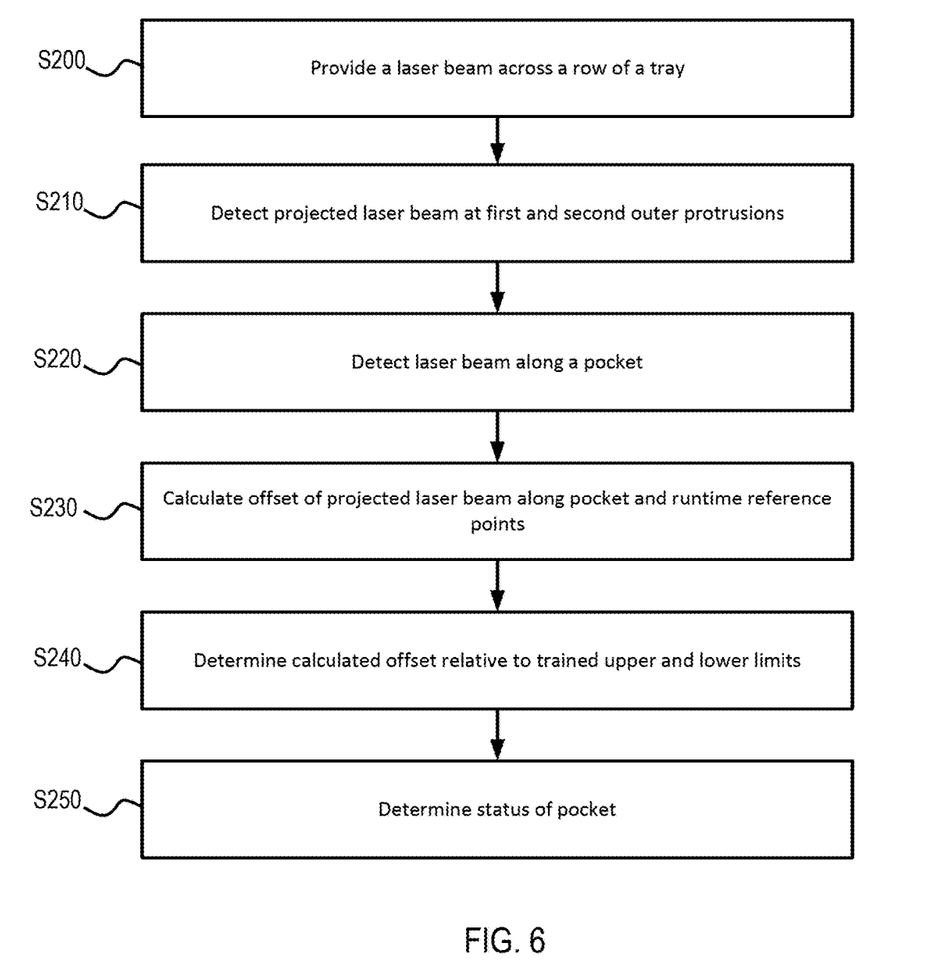
FIG. 6 is a flowchart showing a method for detecting a status of a tray pocket using the detection system of FIG. 1, according to one embodiment.

FIG. 6 is a flowchart of a detection system 100 during runtime of the test handler according to one embodiment. In a step S200, the laser 120 emits a laser beam such that a laser beam having the third optical axis 140' is projected across a row 162a of the tray 160 and the camera 110 images the laser beam across the row 162a. In a step S210, the controller 170 detects the segments of the laser beam projected along the first and second outer protrusions 164a, 164b. These detected segments are then compared to the trained reference points stored for the row 162a during the training process. If the controller 170 determines that the detected segments are offset from the trained reference points within a predetermined tolerance, then the system 100 proceeds with the runtime detection process using the detected segments stored as runtime reference points for that row 162a. If, on the other hand, the controller 170 determines that the detected segments are offset from the trained reference points outside the predetermined tolerance, then the system 100 proceeds with the runtime detection process using the trained reference points as the runtime reference points for that row 162a.

In a step S220, the controller 170 detects the laser beam having the third optical axis 140' projected across a pocket 162. In a step S230, the controller 170 then calculates an offset between the laser beam projected across the pocket 162 and the stored runtime reference points. In a step S240, the controller 170 determines the relative position and angle between the calculated offset and the trained upper and lower limits 141a, 141b. Finally, based on the determined relative position and angle between the calculated offset and the trained upper and lower limits 141a, 141b, the controller 170 may then determine a status of the pocket 162 in a step S250.

Figure 7A:
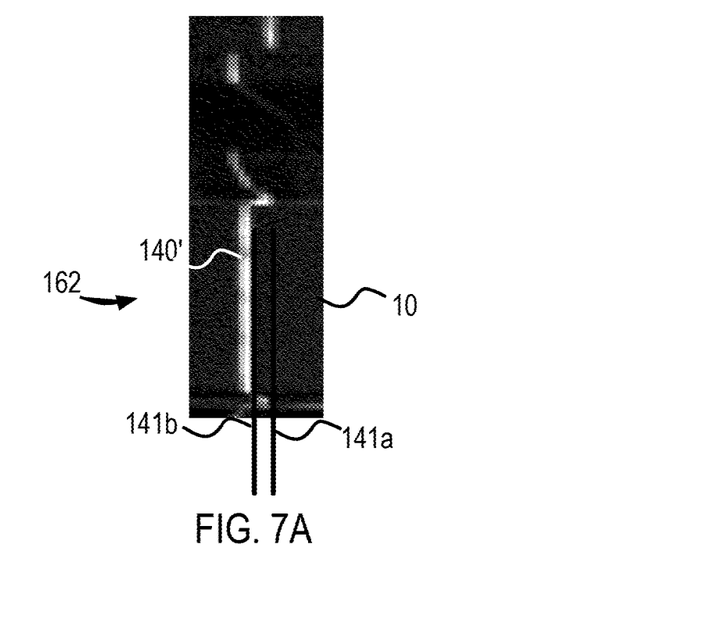
FIGS. 7A-7B are detected statuses of the tray pocket using the method according to FIG. 6.
Figure 7B:
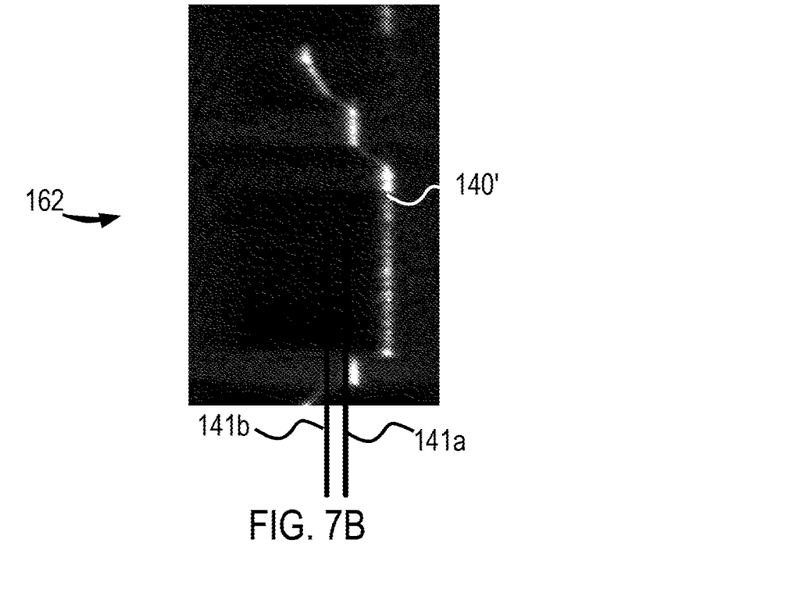

If the position and angle of the calculated offset is within the trained upper and lower limits 141a, 141b determined during step S240, the controller 170 may then determine that the status of the pocket 162 in step S250 is that a device 10 is contained and properly placed within the pocket 162. However, as shown in FIGS. 7A-7B, the controller 170 may determine that the position and angle of the calculated offset is outside of the trained upper and lower limits 141a, 141b. For example, as shown in FIG. 7A, the calculated offset may be shifted outside of the trained lower limit 141b (e.g., to the left in the figure). Depending on the position of the mirror 150 relative to the camera 110, this shift indicates a status of the pocket 162 other than a device 10 that is properly contained within the pocket 162. For example, in the embodiments shown in FIGS. 7A-7B, the mirror 150 is assumed to be positioned on a left side of the camera 110. Thus, as shown in FIG. 7A, when the calculated offset of the projected laser beam within the pocket 10 is shifted to the left such that it is outside the trained lower limit 141b, the controller 170 may determine that the status of the pocket 162 is that the pocket contains two or more stacked devices 10. Moreover, if the calculated offset of the projected laser beam within the pocket 10 is shifted to the right such that it is outside the trained upper limit 141a, as shown in FIG. 7B, the controller 170 may determine that the status of the pocket 162 is empty (i.e., the pocket 162 contains no device). Similar shifts in the calculated offset relative to the upper and lower limits 141a, 141b may indicate other statuses of the pocket 162. For example, a shift outside of the upper limit 141a or lower limit 141b may indicate that the pocket 162 contains a device 10 that is not properly placed (e.g., a partially placed device or a tilted device). In addition, if no laser beam is projected across a pocket 162, such that no shift can be detected by the controller 170, the processor 170 may be configured to determine that the status of the pocket 162 is empty.

Once the status of each of the pockets 162 of the tray 160 has been determined by the detection system 100 using the above process, the controller 170 is configured to output the overall status of the tray 160 to the user through the user interface 180. For example, if the status of each of the pockets 162 is determined to be empty, the controller 170 outputs a passing indication to the user interface 190, indicating to the user that the entire tray 160 is empty and that runtime of the test handler system may proceed. If, on the other hand, one or more pockets 162 are determined to not be empty, the controller 170 outputs a failing indication to the user interface 180, indicating to the user that the entire tray 160 is not empty, which may alert the user to a need for correction.

In certain embodiments, to deal with runtime tray variation and tray tilt variation, during the training process, the camera 110 is configured to first image capture each row 162a of the tray 160. After each row 162a is imaged, the controller 170 detects the projected laser beam on the first and second outer protrusions 164a, 164b for each of the rows and detects the laser beam across each of the pockets 162. The controller 170 determines and stores those rows 162a that have one or more notches 163 such that no laser beam is detected on one or more ends of the row 162a. Once all of the rows 162a have been processed, the controller 170 then interpolates trained reference points for the stored rows 162a having one or more notches 163 based on an average of the detected positions of the projected laser beam for adjacent rows 162a, as discussed above.

For each row 162a, the controller 170 records a set of the detected positions of the projected laser beam for each of the pockets 162 as a curve or fit the set of positions to a second order curve such that a smooth curve is obtained. This stored curve of the position data set is stored as a reference row curve. For a given row 162a, the controller 170 calculates an offset of the detected laser beam projections on the first and second outer protrusions 164a, 164b relative to the reference row curve, which is stored as a reference offset anchor value. This reference offset anchor value may be used to correct for runtime tray tilt variation and height variation present in the tray 160.

To correct for variation during the runtime detection process, the camera 110 may be configured to first image capture each row 162a of the tray 160. After each row 162a is imaged, the controller 170 then detects the projected laser beam on the first and second outer protrusions 164a, 164b for each of the rows and detects the projected laser beam across each of the pockets 162. The controller 170 then calculates an offset of the detected laser beam projections on the first and second outer protrusions 164a, 164b relative to the reference points calculated during training. For those rows 162a having notches 163, the interpolated reference points plus the calculated offset between the detected laser beam project on the first and second outer protrusions 164a, 164b of the previous row 162a relative to its trained reference points may set as the offset detected during runtime. The reference offset anchor value is then used to translate and tilt the reference row curve for a given row 162a, which is then stored by the controller 170 as a corrected row curve. The projected laser beam across a pocket 162a is then compared to the corrected row curve by the controller 170. The trained upper and lower limits 141a, 141b are used to determine the status of each of the pockets 162, as discussed above.

Figure 8:
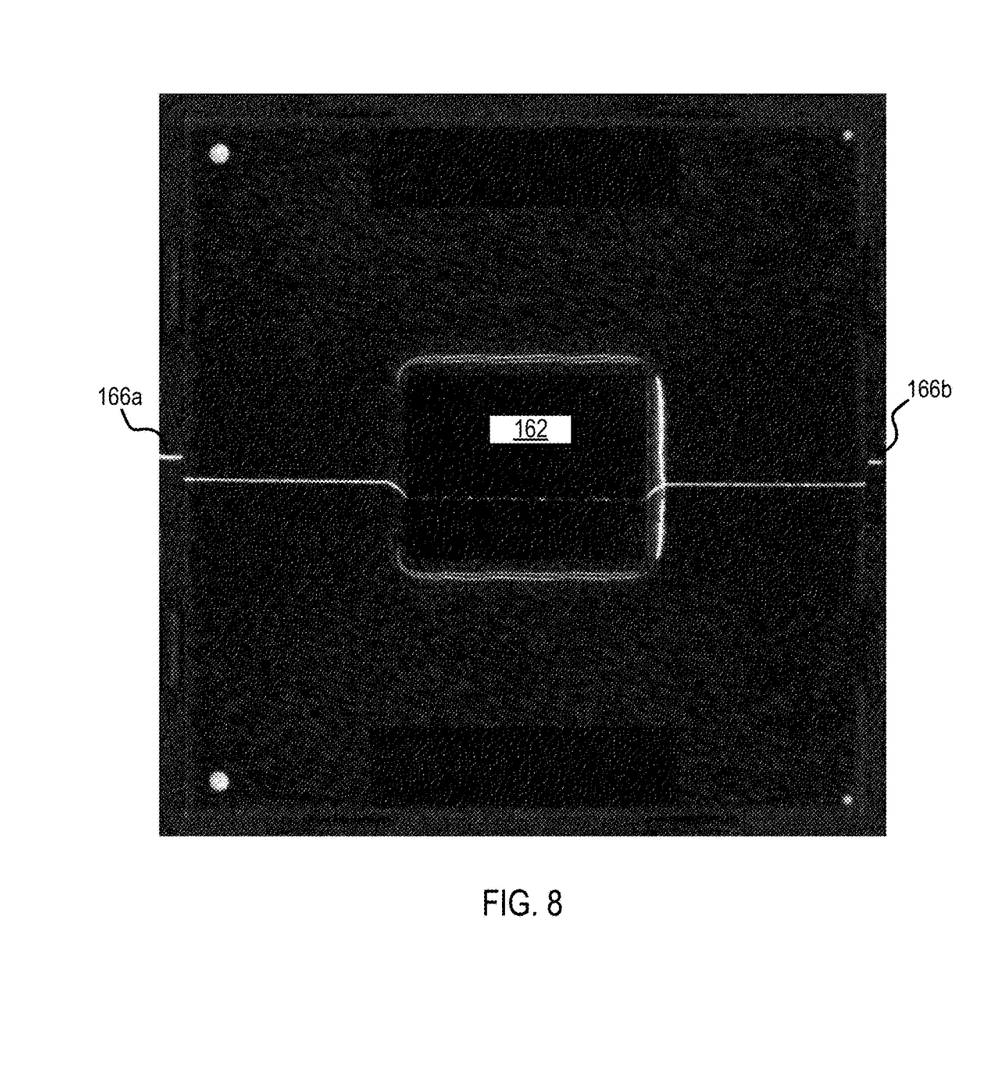
FIG. 8 is a top view of a light line projected onto a pocket of the tray using the detection system of FIG. 1.

If partial tray detection is used for runtime detection, protrusions present at outer edges of a pocket 162 may be used as reference points instead of the first and second outer protrusions 164a, 164b of the tray 160. For example, as shown in FIG. 8, a pocket 162 contains a first edge protrusion 166a along a first side of the pocket 162 and a second edge protrusion 166b along a second side of the pocket 162, which is opposite the first side. The same training process and runtime detection process may be used as detailed above, except that the reference points for the training process and runtime detection process are determined with respect to the position of the projected laser beam on the first and second edge protrusions 166a, 166b of an individual pocket 162.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims.

What is claimed is:

1. A system for detecting a status of a pocket of a tray, the system comprising:
   a tray comprising a plurality of pockets, each of the plurality of pockets being configured to hold an integrated circuit device;
   a vision mechanism configured to image the tray along a first optical axis;
   a light line generator configured to emit a light line along a second optical axis;
   a reflective device configured to reflect the light line onto the tray along a third optical axis, the third optical axis having a different angle relative to the first optical axis than an angle between the first optical axis and the second optical axis; and
   a controller configured to:
      receive an image of the tray from the vision mechanism;
      detect the light line reflected onto the tray along the third optical axis; and
      determine a status of a pocket based on the detected light line along the third optical axis.

2. The system of claim 1, wherein the plurality of pockets is arranged in a plurality of rows and a plurality of columns and the light line along the third optical axis is reflected along a row of the plurality of rows.

3. The system of claim 2, wherein the tray further comprises a first outer protrusion provided at a first end of the plurality of rows and a second outer protrusion provided at a second end of the plurality of rows, the first and second outer protrusions being formed along a length of the plurality of columns.

4. The system of claim 3, wherein the controller is further configured to:
   detect the light line along the third optical axis reflected onto the first outer protrusion and the second outer protrusion;
   detect the light line along the third optical axis reflected onto a surface of the pocket;
   calculate an offset between the detected light line on the first outer protrusion and the second outer protrusion and the detected light line on the surface of the pocket; and
   determine the status of the pocket based on the calculated offset.

5. The system of claim 4, wherein the controller is further configured to:
   set an upper limit position of the light line along the third optical axis reflected on the surface of the pocket;
   set a lower limit position of the light line along the third optical axis reflected on the surface of the pocket; and
   detect a shift of the light line along the third optical axis, the status of the pocket being determined based on the detected shift.

6. The system of claim 3,
   wherein the first outer protrusion and the second outer protrusion are provided with at least one notch such that at least one row of the plurality of rows comprises the at least one notch at an end of the at least one row, and
   wherein the controller is further configured to:
      interpolate a position of the light line along the third optical axis reflected onto the at least one notch based on one or more positions of the detected light line along the third optical axis reflected onto the first outer protrusion or the second outer protrusion of one or more rows adjacent to the at least one row.

7. The system of claim 6, wherein the controller is configured to interpolate the position of the light line along the third optical axis reflected onto the at least one notch based on an average of a first position of the detected light line along the third optical axis reflected onto the first outer protrusion or the second outer protrusion of a first adjacent row and a second position of the detected light line along the third optical axis reflected onto the first outer protrusion or the second outer protrusion of a second adjacent row.

8. The system of claim 1, wherein the status of the pocket is one of an integrated device properly placed in the pocket, a stack of two or more integrated devices placed in the pocket, an integrated device partially placed in the pocket, or an empty pocket.

9. The system of claim 1, wherein the light line generator is a laser.

10. The system of claim 1, wherein the second optical axis is substantially parallel to the first optical axis.

11. The system of claim 10, wherein the first optical axis and the second optical axis are substantially orthogonal to an upper surface of the tray.

12. The system of claim 11, wherein the third optical axis is offset from the first optical axis by an angle of about 35 degrees to about 55 degrees.

13. The system of claim 11, wherein the third optical axis is offset from the first optical axis by an angle of 45 degrees.

14. The system of claim 9, wherein the laser is mounted to the vision mechanism.

15. The system of claim 8, wherein the laser is mounted to a pick-and-place device configured to place a plurality of integrated circuit devices into the plurality of pockets of the tray, and wherein the reflective device is configured to reflect the light line onto the tray along the third optical axis such that the space required to mount the laser to the pick-and-place device is reduced.

16. The system of claim 1, wherein the tray is a JEDEC tray.

17. A method for detecting a status of a pocket of a tray comprising:
   providing a tray comprising a plurality of pockets, each of the plurality of pockets being configured to hold an integrated circuit device;
   providing a vision mechanism configured to image the tray along a first optical axis;
   emitting a light line along a second optical axis;
   reflecting the light line onto the tray along a third optical axis, the third optical axis having a different angle relative to the first optical axis than an angle between the first optical axis and the second optical axis;
   receiving at a controller an image of the tray from the vision mechanism;
   detecting the light line reflected onto the tray along the third optical axis; and
   determining a status of a pocket based on the detected light line along the third optical axis.

18. The method of claim 17, further comprising:
   setting an upper limit position of the light line reflected along the third optical axis projected onto the pocket; and
   setting a lower limit position of the light line reflected along the third optical axis projected onto the pocket;
   wherein the step of determining a status of a pocket comprises detecting a shift of the light line reflected along the third optical axis.

19. The method of claim 17, wherein the third optical axis is offset from the second optical axis by an angle of about 35 degrees to about 55 degrees.

20. The method of claim 17, wherein the second optical axis is substantially orthogonal to an upper surface of the tray.

21. The method of claim 17, wherein the tray comprises a plurality of rows and a plurality of columns, and the light line having the third optical axis is reflected along a row of the plurality of rows.

22. The method of claim 21,
wherein the step of reflecting the light line onto the tray along a third optical axis comprises reflecting a light line having the third optical axis along a first row of the plurality of rows,
wherein the step of detecting the light line reflected onto the tray along the third optical axis comprises detecting the light line having the third optical axis along the first row,
wherein the step of determining a status of a pocket comprises determining a status of each of the plurality of pockets in the first row based on the detected light line reflected along the first row, and
wherein the steps of reflecting the light line, detecting the light line, and determining a status of a pocket are repeated for each row of the plurality of rows.

23. The method of claim 21, wherein the tray further comprises a first outer protrusion disposed at a first end of the plurality of rows and a second outer protrusion disposed at a second end of the plurality of rows, the first and second outer protrusions extending along a length of the plurality of columns.

24. The method of claim 23,
wherein the step of detecting the light line reflected onto the tray comprises detecting the light line reflected along the third optical axis projected onto the first outer protrusion and the second outer protrusion; and
wherein the step of determining a status of a pocket comprises calculating an offset between the detected light line on the first outer protrusion and the second outer protrusion and the detected light line on the pocket.

* * * * *